United States Patent [19]
Chance

[11] Patent Number: 5,564,417
[45] Date of Patent: *Oct. 15, 1996

[54] PATHLENGTH CORRECTED OXIMETER AND THE LIKE

[75] Inventor: Britton Chance, Marathon, Fla.

[73] Assignee: Non-Invasive Technology, Inc., Philadelphia, Pa.

[*] Notice: The term of this patent shall not extend beyond the expiration date of Pat. No. 5,553,614.

[21] Appl. No.: 31,945

[22] Filed: Mar. 16, 1993

Related U.S. Application Data

[63] Continuation-in-part of Ser. No. 645,590, Jan. 24, 1991.

[51] Int. Cl.$^6$ ........................................... A61N 5/02
[52] U.S. Cl. .................. 128/633; 128/637; 128/664; 128/665; 356/39; 356/341; 356/432
[58] Field of Search ..................... 606/2, 10–12; 128/633, 634, 664, 665, 897, 898; 356/4, 5, 51, 39, 72, 319, 320, 323, 341, 432–436, 256

[56] References Cited

U.S. PATENT DOCUMENTS

| | | | |
|---|---|---|---|
| 3,638,640 | 2/1972 | Shaw | 128/633 |
| 4,223,680 | 9/1980 | Jobsis . | |
| 4,281,645 | 8/1981 | Jobsis . | |
| 4,321,930 | 3/1982 | Jobsis et al. . | |
| 4,380,240 | 4/1983 | Jobsis et al. . | |
| 4,510,938 | 4/1985 | Jobsis et al. . | |
| 4,714,341 | 12/1987 | Hamaguri et al. . | |
| 4,800,495 | 1/1989 | Smith . | |
| 4,800,885 | 1/1989 | Johnson . | |
| 4,805,623 | 2/1989 | Jobsis . | |
| 4,824,242 | 4/1989 | Frick et al. . | |
| 4,827,934 | 5/1989 | Parker | 128/633 |
| 4,972,331 | 11/1990 | Chance . | |
| 5,119,815 | 6/1992 | Chance . | |
| 5,167,230 | 12/1992 | Chance . | |
| 5,187,672 | 2/1993 | Chance et al. . | |

FOREIGN PATENT DOCUMENTS

WO92/20273 11/1992 WIPO.

OTHER PUBLICATIONS

Chance et al., "Photon Migration in Muscle and Brain", *Photon Migration in Tissues*, Academic Press/ New York 1989.

Chance, "Rapid and Sensitive Apectrophotometry, I. The Accelerated and Stopped–Flow Methods for the Measurement of the Reaction Kinetics, etc.", *The Review of Scientific Instruments*, 22:619–638 (1951).

Cui et al., "Experimental Study of Migration Depth for the Photons Measured at Sample Surface", *Proceedings of Time–Resolved Spectroscopy and Imaging of Tissues*, SPIE, 1413: 180–191 (1991).

Lakowicz, "Gigahertz Frequency–Domain Fluorometry: Resolution of Complex Intensity Decays, Picosecond Processes and Future Developments", *Photon Migration in Tissues*, pp. 169–185.

(List continued on next page.)

*Primary Examiner*—David M. Shay
*Attorney, Agent, or Firm*—Fish & Richardson P.C.

[57] ABSTRACT

A pathlength corrected spectrophotometer for tissue examination includes an oscillator for generating a carrier waveform of a selected frequency, an LED light source for generating light of a selected wavelength that is intensity modulated at the selected frequency introduced to a subject, and a photodiode detector for detecting light that has migrated in the tissue of the subject. The spectrophotometer also includes a phase detector for measuring a phase shift between the introduced and detected light, a magnitude detector for determination of light attenuation in the examined tissue, and a processor adapted to calculate the photon migration pathlength and determine a physiological property of the examined tissue based on the pathlength and on the attenuation data.

30 Claims, 7 Drawing Sheets

OTHER PUBLICATIONS

Sevick et al., "Analysis of absorption, scattering, and hemoglobin saturation using phase modulation spectroscopy", *Proceedings of Time–Resolved Spectroscopy and Imaging Tissues*, SPIE, 1431:264–275 (1991).

Sevick et al., "Photon migration in a model of the head measured using time–and frequency–domain, etc.", *Proceedings of Time–Resolved Spectroscopy and Imaging Tissues*, SPIE, 1431:84–96 (1991).

Sevick et al., "Quantitation of Time– and Frequency–Resolved Optical Spectra for the Determination of Tissue Oxygenation", *Analytical Biochemistry*, 195:001–0022 (1991).

Van der Zee et al., "Computed Point Spread Functions for Light in Tissue Using a Measured Volume Scattering Function", *Advances in Experimental Medicine and Biology: Oxygen Transport to Tissue X*, 222:191–197 (1988).

Weng et al., "Measurement of Biological Tissue Metabolism Using Phase Modulation Spectroscopic Technology", *Proceedings of Time–Resolved Spectroscopy and Imaging of Tissues*, SPIE, 1431: 161–170 (1991).

PATHLENGTH CORRECTED OXIMETER AND THE LIKE

CROSS REFERENCE TO RELATED APPLICATION

This application is a continuation-in-part of application Ser. No. 07/645,590 filed Jan. 24, 1991 incorporated by reference as if fully set forth herein.

BACKGROUND OF THE INVENTION

The present invention relates to a wearable tissue spectrophotometer for in vivo examination of tissue of a specific target region.

Continuous wave (CW) tissue oximeters have been widely used to determine in vivo concentration of an optically absorbing pigment (e.g., hemoglobin, oxyhemoglobin) in biological tissue. The CW oximeters measure attenuation of continuous light in the tissue and evaluate the concentration based on the Beer Lambert equation or modified Beer Lambert absorbance equation. The Beer Lambert equation (1) describes the relationship between the concentration of an absorbent constituent (C), the extinction coefficient ($\epsilon$), the photon migration pathlength $<L>$, and the attenuated light intensity ($I/I_o$).

$$\frac{\log[I/I_o]}{<L>} = \Sigma \epsilon_i C_i \qquad (1)$$

The CW spectrophotometric techniques can not determine $\epsilon$, C, and $<L>$ at the same time. If one could assume that the photon pathlength were constant and uniform throughout all subjects, direct quantitation of the constituent concentration (C) using CW oximeters would be possible.

In tissue, the optical migration pathlength varies with the size, structure, and physiology of the internal tissue examined by the CW oximeters. For example, in the brain, the gray and white matter and the structures thereof are different in various individuals. In addition, the photon migration pathlength itself is a function of the relative concentration of absorbing constituents. As a result, the pathlength through an organ with a high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. Thus, where possible, it is advantageous to measure the pathlength directly when quantifying the hemoglobin concentration in tissue.

SUMMARY OF THE INVENTION

In one aspect, the present invention is a pathlength corrected oximeter that utilizes principles of continuous wave spectroscopy and phase modulation spectroscopy. The oximeter is a compact unit constructed to be worn by a subject on the body over long periods of activity. The oximeter is also suitable for tissue monitoring in critical care facilities, in operating rooms while undergoing surgery or in trauma related situations.

The oximeter is mounted on a body-conformable support structure placed on the skin. The support structure encapsulates several light emitting diodes (LEDs) generating light of different wavelengths introduced into the examined tissue and several photodiode detectors with interference filters for wavelength specific detection. Since both the LEDs and the photodiodes are placed directly on the skin, there is no need to use optical fibers. The distance between the LEDs and the diode detectors is selected to examine a targeted tissue region. The support structure also includes a conformable barrier, located between the LEDs and the diode detectors, designed to reduce detection of light that migrates subcutaneously from the source to the detector. The support structure may further include means for preventing escape of photons from the skin without being detected; the photon escape preventing means are located around the LEDs and the photodiode detectors.

The LEDs, the diode detectors, and the electronic control circuitry of the oximeter are powered by a battery pack adapted to be worn on the body or by the standard 50/60 Hz supply. The electronic circuitry includes a processor for directing operation of the sources, the detectors and for directing the data acquisition and processing. The data may be displayed on a readout device worn by the user, sent by telemetry to a remote location or accumulated in a memory for later use.

The oximeter is adapted to measure the attenuation of light migrating from the source to the detector and also to determine the average migration pathlength. The migration pathlength and the intensity attenuation data are then used for direct quantitation of a tissue property.

In another aspect, the invention is a spectrophotometer for tissue examination utilizing a measured average pathlength of migrating photons, including an oscillator adapted to generate a carrier waveform of a selected frequency comparable to an average migration time of photons scattered in tissue on paths from an optical input port to an optical detection port; a light source, operatively connected to the oscillator, adapted to generate light of a selected wavelength that is intensity modulated at the frequency and introduced to a subject at the input port; a photodiode detector adapted to detect, at the detection port, light of the selected wavelength that has migrated in the tissue of the subject between the input and detection ports; a phase detector, operatively connected to receive signals from the oscillator and the diode detector, adapted to measure a phase shift between the introduced and the detected light; and a processor adapted to calculate pathlength based on the phase shift, and determine a physiological property of the examined tissue based on the pathlength.

In another aspect, the invention is a spectrophotometer for tissue examination utilizing a measured average pathlength of migrating photons, including an oscillator adapted to generate a carrier waveform of a selected frequency comparable to an average migration time of photons scattered in tissue on paths from an optical input port to an optical detection port; a light source, operatively connected to the oscillator, adapted to generate light of a selected wavelength that is intensity modulated at the frequency and introduced to a subject at the input port; a photodiode detector adapted to detect, at the detection port, light of the selected wavelength that has migrated in the tissue of the subject between the input and detection ports; a phase splitter adapted to produce, based on the carrier waveform, first and second reference phase signals of predefined substantially different phase; first and second double balanced mixers adapted to correlate the reference phase signals and signals of the detected radiation to produce therefrom a real output signal and an imaginary output signal, respectively; and a processor adapted to calculate, on the basis of the real output signal and the imaginary output signal, a phase shift between the introduced light and the detected light, and determine a physiological property of the examined tissue based on the phase shift.

In another aspect, the invention is a spectrophotometer for tissue examination utilizing a measured average pathlength of migrating photons, comprising a first oscillator adapted to generate a carrier waveform of a first selected frequency comparable to an average migration time of photons scattered in tissue on paths from an optical input port to an optical detection port; a light source, operatively connected to the oscillator, adapted to generate light of a selected wavelength, intensity modulated at the first frequency, that is introduced to a subject at the input port; a photodiode detector adapted to detect, at the detection port, light of the wavelength that has migrated in the tissue of the subject between the input and detection ports, the detector producing a detection signal at the first frequency corresponding to the detected light; a second oscillator adapted to generate a carrier waveform of a second frequency that is offset on the order of $10^4$ Hz from the first frequency; a reference mixer, connected to the first and second oscillators, adapted to generate a reference signal of a frequency approximately equal to the difference between the first and second frequencies; a mixer connected to receive signals from the second oscillator and the detection signal and adapted to convert the detection signal to the difference frequency; a phase detector, operatively connected to receive signals from the reference mixer and the converted detection signal, adapted to measure a phase shift between the introduced light and the detected light; and a processor adapted to calculate the pathlength based on the phase shift, and to determine a physiological property of the examined tissue based on the pathlength.

Preferred embodiments of these aspects may include one or more of the following features.

The spectrophotometer may further include a magnitude detector, connected to the photodiode detector, adapted to measure magnitude of the detected light, and the processor is further adapted to receive the magnitude for determination of the physiological property.

The spectrophotometer may further include a low frequency oximeter circuit, switchably connected to the source and the photodiode, adapted to determine absorption of light at the wavelength; and the processor is further adapted to receive absorption values from the oximeter circuit for determination of the physiological property.

The spectrophotometer may further include two automatic gain controls adapted to level signals corresponding to the introduced light and the detected light, both the leveled signals being introduced to the phase detector.

The photodiode detector may further include a substantially single wavelength filter.

The spectrophotometer may further include a second light source, operatively connected to the oscillator, adapted to generate light of a second selected wavelength that is intensity modulated at the first frequency, the radiation being introduced to a subject at a second input port; the photodiode detector further adapted to detect alternately, at the detection port, light of the first and second wavelengths that have migrated in the tissue of the subject between the first and the second input ports and the detection port, respectively; the phase detector further adapted to receive alternately signals corresponding to the detected first and second wavelengths; and the processor further adapted to receive alternately phase shifts from the phase detector, the phase shifts being subsequently used for determination of the physiological property of the tissue.

The spectrophotometer may further include a second light source, operatively connected to the oscillator, adapted to generate light of a second selected wavelength that is intensity modulated at the first frequency, the radiation being introduced to a subject at a second input port; a second photodiode detector adapted to detect, at a second detection port, light of the second wavelength that has migrated in the tissue of the subject between the second input port and the second detection port, respectively; a second phase detector, operatively connected to receive a reference signal and a detection signal from the third diode detector, adapted to measure a phase shift between the introduced and the detected light at the second wavelength; and the processor further adapted to receive a second phase shift at the second wavelength, the first and second phase shifts being subsequently used for determination of the physiological property of the tissue.

The two wavelength spectrophotometer may further include a third light source, operatively connected to the oscillator, adapted to generate light of a third selected wavelength that is intensity modulated at the first frequency, the radiation being introduced to a subject at a third input port; a third photodiode detector adapted to detect, at a third detection port, light of the third wavelength that has migrated in the tissue of the subject between the third input port and the third detection port, respectively; a third phase detector, operatively connected to receive a reference signal and a detection signal from the third diode detector, adapted to measure a phase shift between the introduced and the detected light at the third wavelength; and the processor further adapted to receive phase shifts from the phase detector, the first second and third phase shifts being subsequently used for determination of the physiological property of the tissue.

The two or three wavelength spectrophotometer may further include a first, a second (or a third) magnitude detector connected to the first, second (or third) photodiode detectors, respectively, the magnitude detectors being adapted to measure magnitude of the detected light at each of the wavelengths; and the processor further adapted to receive the magnitudes for determination of the physiological property of the tissue.

The light source may be a light emitting diode for generating light of a selected wavelength in the visible or infra-red range.

The photodiode detector may be a PIN diode or an avalanche diode.

The examined physiological property of the tissue may be hemoglobin oxygenation, myoglobin, cytochrome iron and copper, melanin, glucose or other.

DESCRIPTION OF THE PREFERRED EMBODIMENTS

One preferred embodiment of the pathlength corrected oximeter utilizes three LEDs for generation of light at three selected wavelengths intensity modulated at a frequency of 50.1 MHz and coupled directly to the examined tissue. At each wavelength, the introduced light is altered by the tissue and is detected by a wide area photodiode placed against the skin. The introduced and detected radiations are compared to determine their relative phase shift that corresponds to an average pathlength of the migrating photons and, furthermore, the light attenuation is determined.

Figure 1:
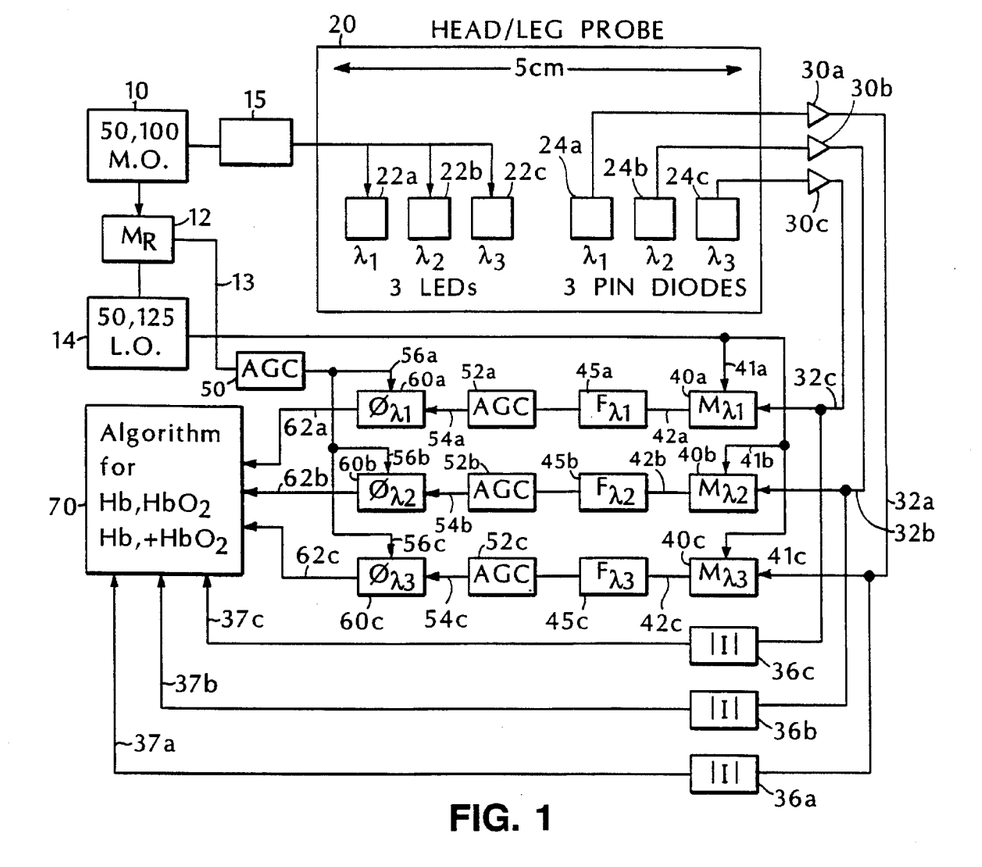
FIG. 1 is a block diagram of a pathlength corrected oximeter in accordance with the present invention.

Referring to FIG. 1, the oximeter includes a master oscillator 10 operating at 50.1 MHz connected to a power amplifier 15 of sufficient output power to drive LEDs 22a, 22b, and 22c (for example HLP 20RG or HLP 40RG made by Hitachi) that emit 760 nm, 840 nm, and 905 nm (or 950 nm) light, respectively. A second local oscillator 14 operating at 50,125 MHz and mixer 12 are used to generate a reference frequency 13 of 25 kHz. Each LED directly positioned on the skin has an appropriate heat sink to eliminate uncomfortable temperature increases that could also alter blood perfusion of the surrounding tissue. Three PIN diode detectors 24a, 24b, and 24c are placed at a distance of approximately 5 cm from the LEDs and have a detection area of about 1 cm². Photons migrating a few centimeters deep into the tissue are detected by the respective PIN diodes. The source-detector separation can be increased or decreased to capture deeper or shallower migrating photons. The signals from PIN diodes 24a, 24b, and 24c are amplified by preamplifiers 30a, 30b, and 30c, respectively.

The amplified signals (32a, 32b, 32c) are sent to magnitude detectors 36a, 36b, and 36c and to mixers 40a, 40b, and 40c, respectively. The magnitude detectors are used to determine intensity values of detected signals at each wavelength to be used in Eq. 1. Each mixer, connected to receive a 50,125 MHz reference signal (41a, 41b, 41c) from local oscillator 14, converts the detection signal to a 25 kHz frequency signal (42a, 42b, 42c). The mixers are high dynamic range frequency mixers, model SRA-1H, commercially available from Mini-Circuits (Brooklyn N.Y.). The detection signals (42a, 42b, and 42c) are filtered by filters 45a, 45b, 45c, respectively.

Phase detectors 60a, 60b, and 60c are used to determine phase shift between the input signal and the detected signal at each wavelength. Each phase detector receives the 25 kHz detection signal (54a, 54b, 54c) and the 25 kHz reference signal (56a, 56b, 56c), both of which are automatically leveled by automatic gain controls 50 and 52 to cover the dynamic range of signal changes. Phase detectors 60a, 60b, and 60c generate phase shift signals (62a, 62b, 62c) corresponding to the migration delay of photons at each wavelength. Each phase shift signal is proportional to the migration pathlength used in calculation algorithms performed by processor 70.

Figure 2:
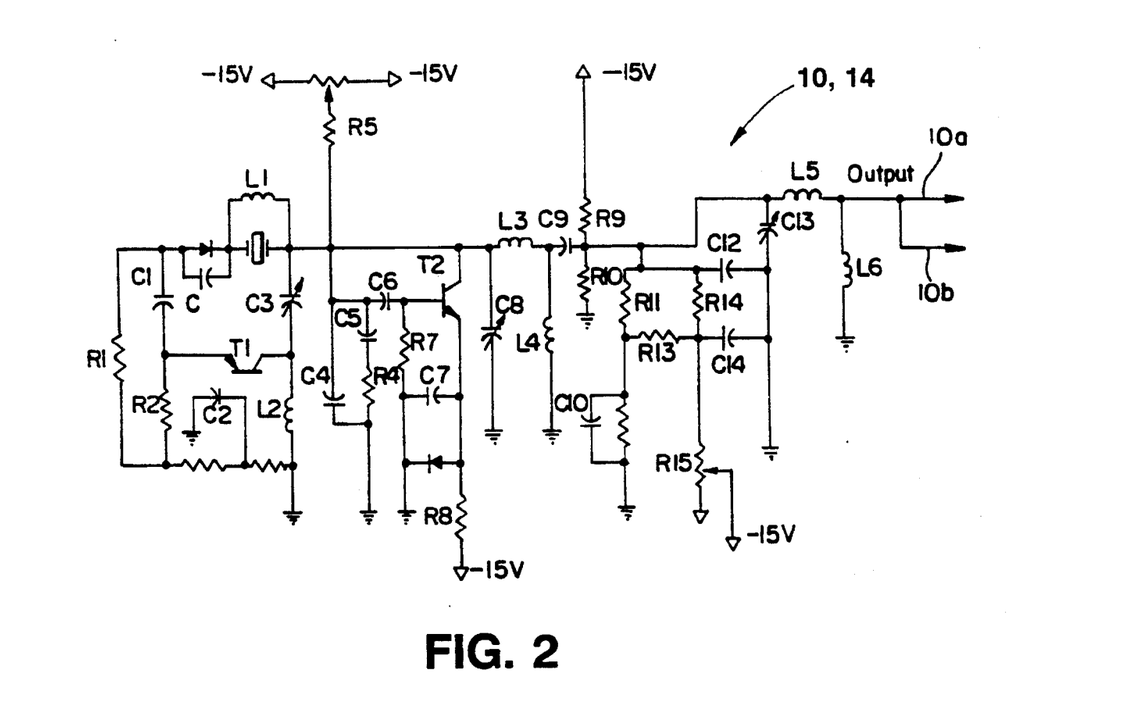
FIG. 2 is a schematic circuit diagram of a 50.1 MHz (50.125 MHz) oscillator used in the oximeter of FIG. 1.

FIG. 2 shows a schematic circuit diagram of a precision oscillator used as the 50.1 MHz master oscillator 10 and 50.125 MHz local oscillator 14. The oscillator crystals are neutralized for operation in the fundamental resonance mode; this achieves long-term stability. Both oscillators are thermally coupled so that their frequency difference is maintained constant at 25 kHz if a frequency drift occurs.

Figure 3:
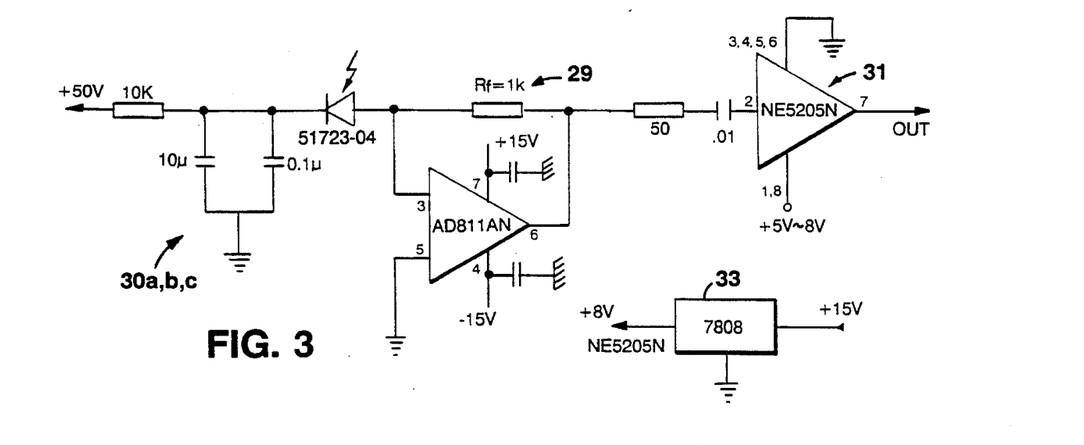
FIG. 3 is a schematic circuit diagram of a PIN diode and a preamplifier used in the oximeter of FIG. 1.
Figure 4:
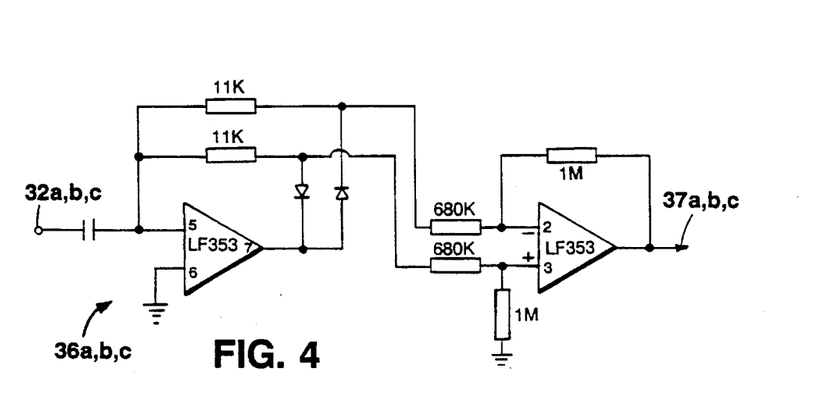
FIG. 4 is a schematic circuit diagram of a magnitude detector used in the oximeter of FIG. 1.

PIN diodes 24a, 24b, and 24c are directly connected to their respective preamplifiers 30a, 30b, and 30c, as shown in FIG. 3. The oximeter uses PIN silicon photodiodes S1723-04 with 10 mm×10 mm sensitive area and spectral response in the range of 320 nm to 1060 nm. The detection signal is amplified by stages 29 and 31, each providing about 20 dB amplification. The NE5205N operational amplifier is powered at +8 V to operate in a high gain regime. The 8 V signal is supplied by a voltage regulator 33. The amplified detection signals (32a, 32b, and 32c) are sent to magnitude detectors 36a, 36b, and 36c, shown in FIG. 4. The magnitude values (37a, 37b, and 37c) are sent to processor 70 that calculates the light attenuation ratio or logarithm thereof as shown Eq. 1.

Figure 5:
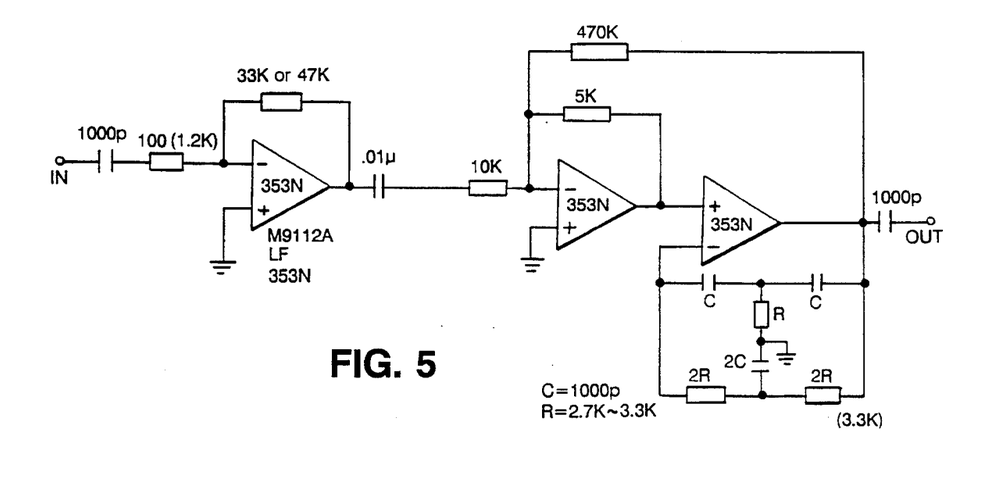
FIG. 5 is a schematic circuit diagram of a 25 kHz filter used in the oximeter of FIG. 1.

Also referring to FIG. 5, the AGC circuit uses MC 1350 integrated circuit for amplification that maintains the input signal of phase detector 60 at substantially constant levels. The amount of gain is selected to be equal for AGCs, 50 and 52. The signal amplitude is controlled by a feedback network 53. The AGCs provide a substantially constant amplitude of the detected and reference signals to eliminate variations in the detected phase shift due to cross talk between amplitude and phase changes in the phase detector.

Figure 6:
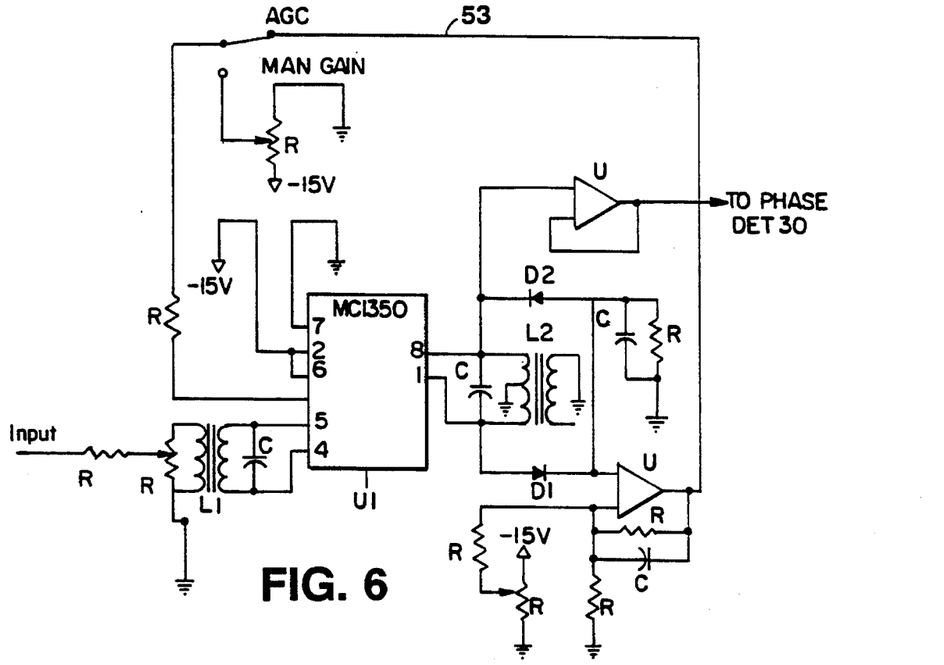
FIG. 6 is a schematic diagram of an AGC circuit of the oximeter of FIG 1.
Figure 7:
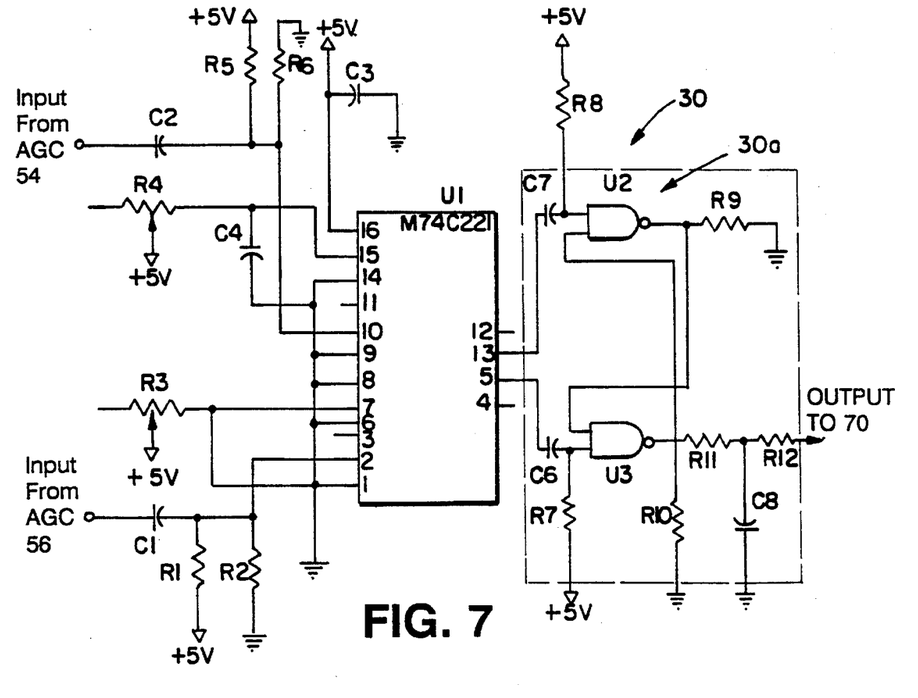
FIG. 7 is a schematic circuit diagram of a phase detector of the oximeter of FIG. 1.

Referring to FIG. 6, each phase detector includes a Schmitt trigger that converts the substantially sinusoidal detection signal (54a, 54b, 54c) and reference signal (56a, 56b, 56c) to square waves. The square waves are input to a detector that has complementary MOS silicon-gate transistors. The phase shift signal is sent to processor 70.

The oximeter is calibrated by measuring the phase shift for a selected distance in a known medium, i.e., using a standard delay unit, and by switching the length of a connector wire to change the electrical delay between master oscillator 10 and local oscillator 14.

Figure 8A:
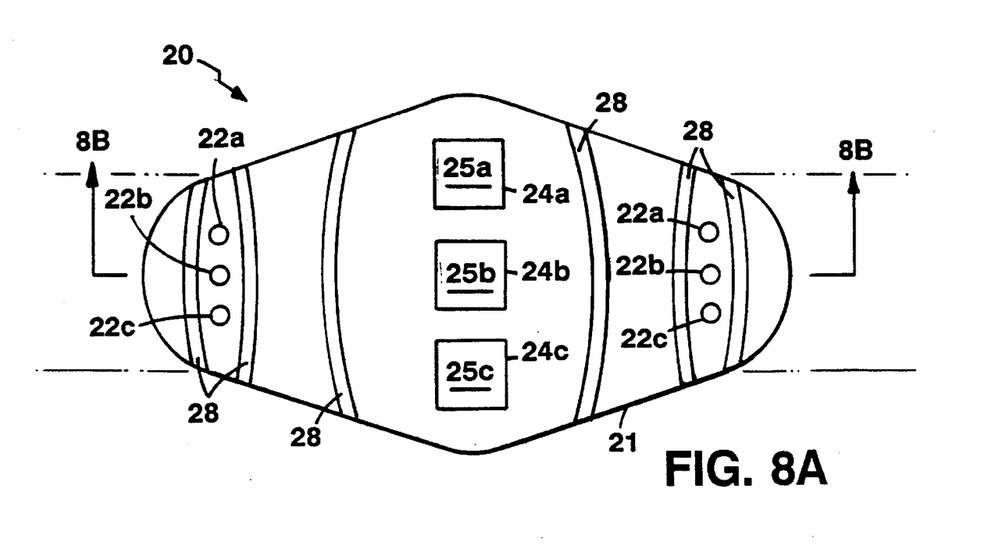
FIG. 8A is a plan view of a source-detector probe of the oximeter.
Figure 8B:
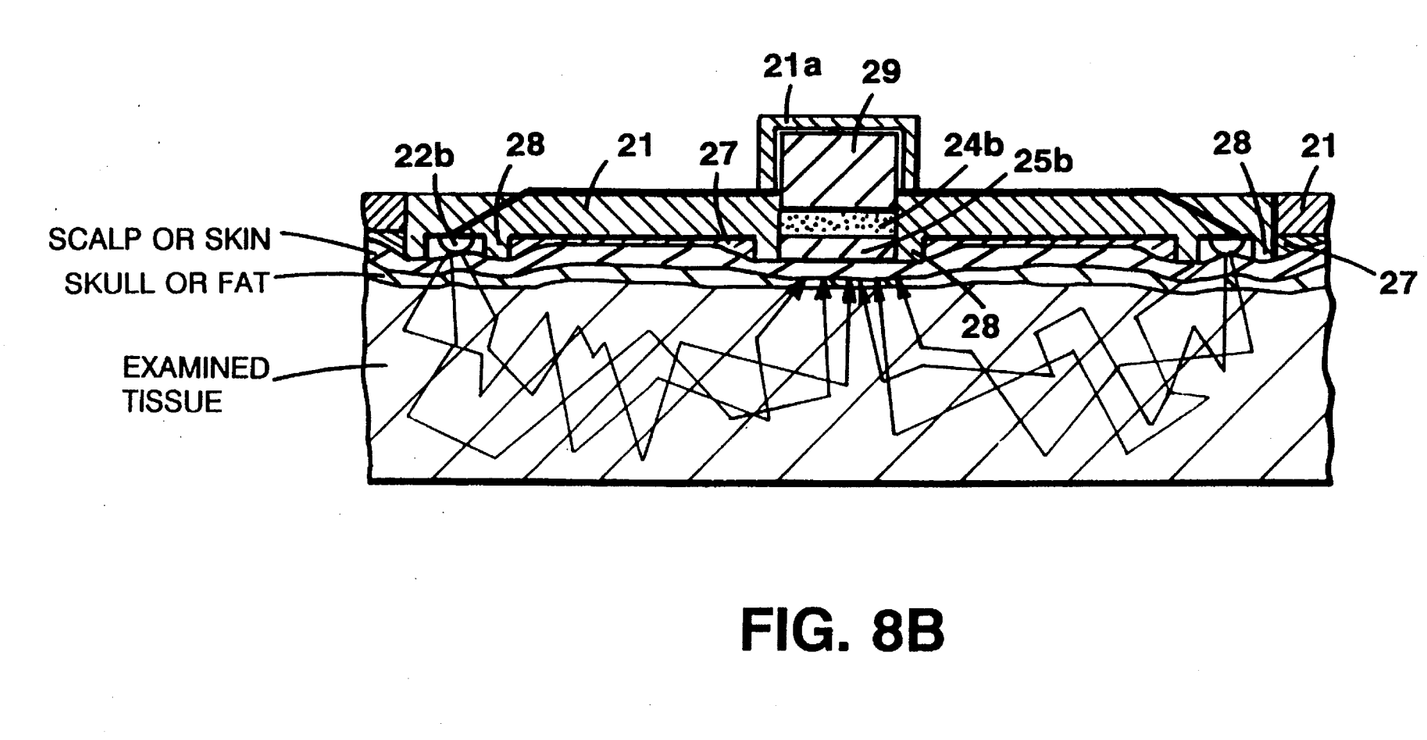
FIG. 8B is a transverse cross-sectional view taken on lines 8B of FIG. 8A further showing the photon migration.

Referring to FIGS. 8A and 8B source-detector probe 20 includes several LEDs (22a, 22b, 22c) of selected wavelengths and PIN photodiodes (24a, 24b, 24c) mounted in a body-conformable support structure 21. Structure 21 also includes a photon escape barrier 27 made of a material with selected scattering and absorption properties (for example, styrofoam) designed to return escaping photons back to the examined tissue. The support structure further includes a second conformable barrier 28, located between the LEDs and the diode detectors, designed to absorb photons directly propagating from the source to the detector and thus prevent detection of photons that migrate subcutaneously. Support structure 21 also includes electronic circuitry 29 encapsulated by an electronic shield 21a.

Each PIN diode is provided with an evaporated single wavelength film filter (25a, 25b, 25c). The filters eliminate the cross talk of different wavelength signals and allow continuous operation of the three light sources, i.e., no time sharing is needed.

The use of photodiode detectors has substantial advantages when compared with the photomultiplier tube used in standard phase modulation systems. The photodiodes are placed directly on the skin, i.e., no optical fibers are needed.

Furthermore, there is no need to use a high voltage power supply that is necessary for the photomultiplier tube. The photodiodes are much smaller and are easy to place close to the skin. Advantages of the photomultiplier tube are a huge multiplication gain and a possibility of direct mixing at the photomultiplier; this cannot be achieved directly by a photodiode. This invention envisions the use of several different photodiodes such as PIN diode, avalanche diode, and other.

The processor uses algorithms that are based on equations described by E. M. Sevick et al. in "Quantitation of Time- and Frequency-Resolved Optical Spectra for the Determination of Tissue Oxygenation" published in Analytical Biochemistry 195, 330 Apr. 15, 1991 which is incorporated by reference as if fully set forth herein.

At each wavelength, the phase shift ($\theta^\lambda$) (62a, 62b, 62c) is used to calculate the pathlength as follows:

$$\theta^\lambda = \tan^{-1} \pi f \langle t^\lambda \rangle = \tan^{-1} \frac{2\pi f \langle L^\lambda \rangle}{c} \approx \frac{2\pi f \langle L^\lambda \rangle}{c} \quad (2)$$

wherein f is modulation frequency of the introduced light which is in the range of 10 MHz to 100 MHz; $t^\lambda$ is the photon migration delay time; c is the speed of photons in the scattering medium; and $L^\lambda$ is the migration pathlength.

Equation (2) is valid at low modulation frequencies, i.e., $2\pi f \ll \mu_a \cdot c$. The modulation frequency of 50 MHz was selected due to the frequency limitation of the LEDs and photodiodes. However, for faster LEDs and photodiodes it may be desirable to use higher modulation frequencies that increase the phase shift. At high modulation frequencies, i.e., $2\pi f \gg \mu_a \cdot c$, the phase shift is no longer proportional to the mean time of flight $\langle t \rangle$.

$$\theta^\lambda = a\rho \sqrt{(1-g)\mu_s f} \left\{ 1 - \frac{\mu_a^\lambda c}{4\pi f} \right\} \quad (3)$$

wherein $\rho$ is the source-detector separation; $(1-g)\mu_s$ is effective scattering coefficient; f is modulation frequency and $\mu_a^\lambda$ is absorption coefficient at wavelength $\lambda$. At two wavelength, the ratio of absorption coefficients is determined as follows:

$$\frac{\mu_a^{\lambda 1}}{\mu_a^{\lambda 2}} = \frac{\theta^{\lambda 1} - \theta_o^{\lambda 1}}{\theta^{\lambda 2} - \theta_o^{\lambda 2}} \quad (4)$$

wherein $\theta_0^\lambda$ represents background scattering and absorption.

The wavelengths are in the visible and infra-red range and are selected to have absorbance sensitive (or insensitive) to various tissue components such as water, cytochrome iron and copper, oxy- and deoxygenated forms of hemoglobin, myoglobin, melanin, glucose and other.

For oxygenated and deoxygenated hemoblogin, the absorption coefficient written in terms of Beer Lambert relationship is as follows:

$$\mu_a^{\lambda 1} = \epsilon_{Hb}^{\lambda 1} [Hb] + \epsilon_{Hbo}^{\lambda 1} [HbO_2] + \alpha^{\lambda 1} \quad (5)$$

wherein $\epsilon_{Hb}^{\lambda 1}$ and $\epsilon_{HbO}^{\lambda 1}$ are extinction coefficients for hemoglobin and deoxyhemoglobin that can be stored in a look up table; [Hb], [HbO$_2$] are the tissue concentration of hemoglobin and oxyhemoglobin, respectively; $\alpha^{\lambda 1}$ is background absorbance. The hemoglobin saturation is conventionally defined as follows:

$$Y = \frac{[HbO_2]}{[Hb] + [HbO_2]} \quad (6)$$

For a three wavelength measurement, the hemoglobin saturation can be calculated using Eqs. (5) and (6) as follows:

$$Y = \frac{a(\epsilon_{Hb}^{\lambda 3} - \epsilon_{Hb}^{\lambda 2}) - (\epsilon_{Hb}^{\lambda 1} - \epsilon_{Hb}^{\lambda 2})}{[(\epsilon_{HbO_2}^{\lambda 1} - \epsilon_{HbO_2}^{\lambda 2}) - (\epsilon_{Hb}^{\lambda 1} - \epsilon_{Hb}^{\lambda 2})] - a[(\epsilon_{HbO_2}^{\lambda 3} - \epsilon_{HbO_2}^{\lambda 2}) - (\epsilon_{Hb}^{\lambda 3} - \epsilon_{Hb}^{\lambda 2})]} \quad (7)$$

where $$a = \frac{\mu_a^{\lambda 1} - \mu_a^{\lambda 2}}{\mu_a^{\lambda 3} - \mu_a^{\lambda 2}}$$

Thus, processor 70 determines Y based on Eq. (7) using Eq. (2) to determine the average migration pathlength L that is then used in Eq. (1) and to determine $\mu_a^\lambda$ for each wavelength $\lambda_1$, $\lambda_2$, $\lambda_3$.

Figure 8C:
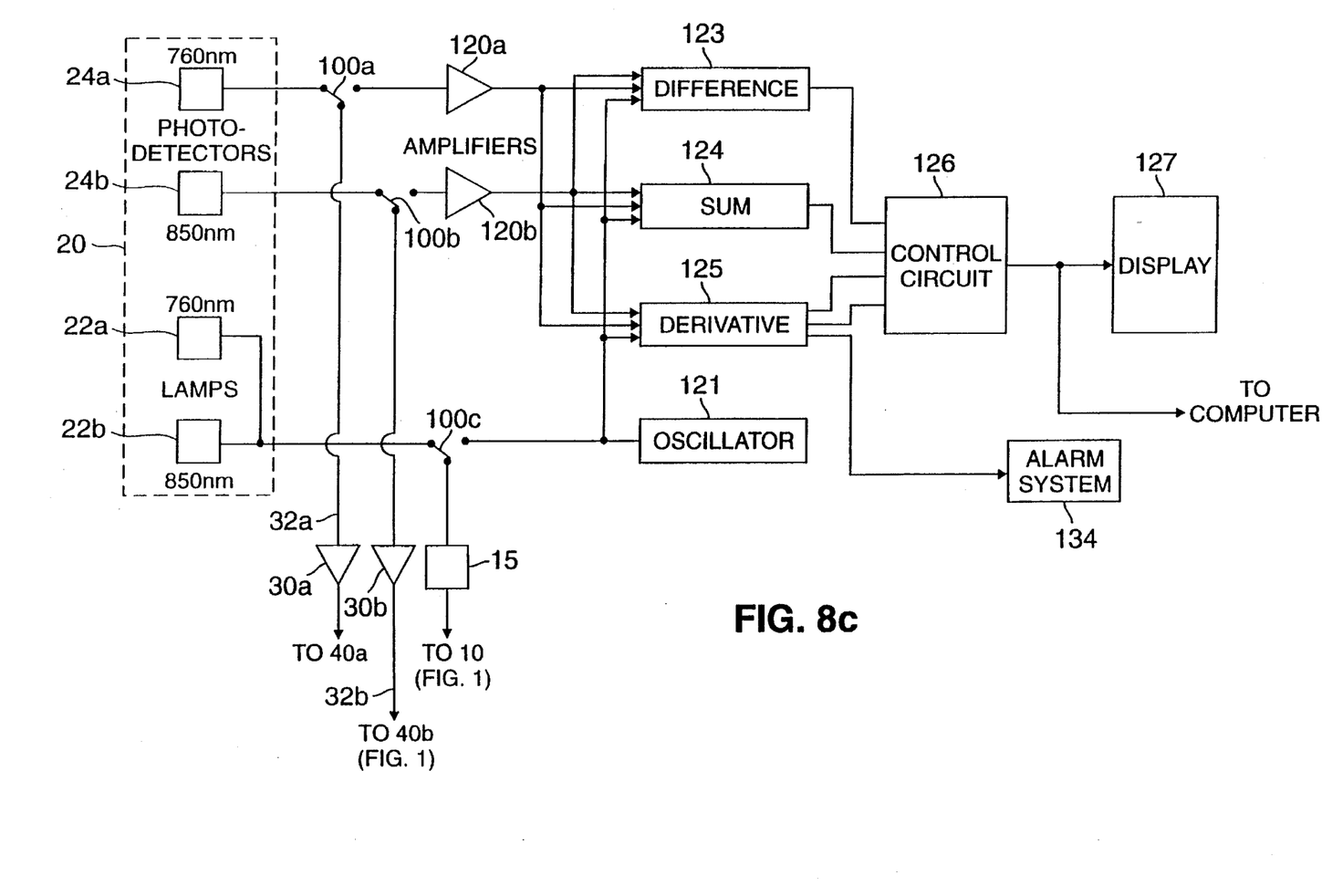
FIG. 8C is a block diagram of another embodiment depicting the source-detector probe of the oximeter switchably connected to a low frequency oximeter.

Referring to FIG. 8C in another embodiment, the spectrophotometer's electronics includes a low frequency module, as shown for example in FIGS. 2 and 4 of U.S. Pat. No. 5,167,230, and a high frequency module switchably coupled to the same source-detector probe 20. The low frequency module and the arrangement of the source-detector probe are substantially similar to the hemoglobinometer described in a copending U.S. patent application Ser. No. 701,127 filed May 16, 1991 which is incorporated by reference as if fully set forth herein. The low frequency module corresponds to a standard oximeter with modulation frequencies in the range of a few hertz to $10^4$ hertz and is adapted to provide intensity attenuation data at two or three wavelengths. FIG. 8C depicts an analog embodiment of the low frequency oximeter coupled to source-detector probe 20 by switches 100a, 100b, and 100c. The light detected by photodetectors 24a and 24a is amplified by amplifiers 120a and 120b and sent to three manipulative circuits that take the difference (123), the sum (124) and the derivative (125) of the signal. The difference circuit (123) subtracts 760 nm minus 850 nm to obtain a signal representing deoxygenation. The sum circuit (124) takes a weighted sum of the 760 nm and 850 nm signals that is a representative of the blood volume changes in the tissue. The derivative circuit takes the simple derivative to show the rate of change of both of the signals. The derivative triggers alarm circuitry 134 based upon established standards, for example, in monitoring aviators for possible black-out conditions and for apnea. Then, the LEDs are switched to the high frequency phase modulation unit, similar to the unit of FIG. 1, which determines the average pathlength at each wavelength. The attenuation and pathlength data are sent to processor 70 for determination of a physiological property of the examined tissue.

Figure 9:
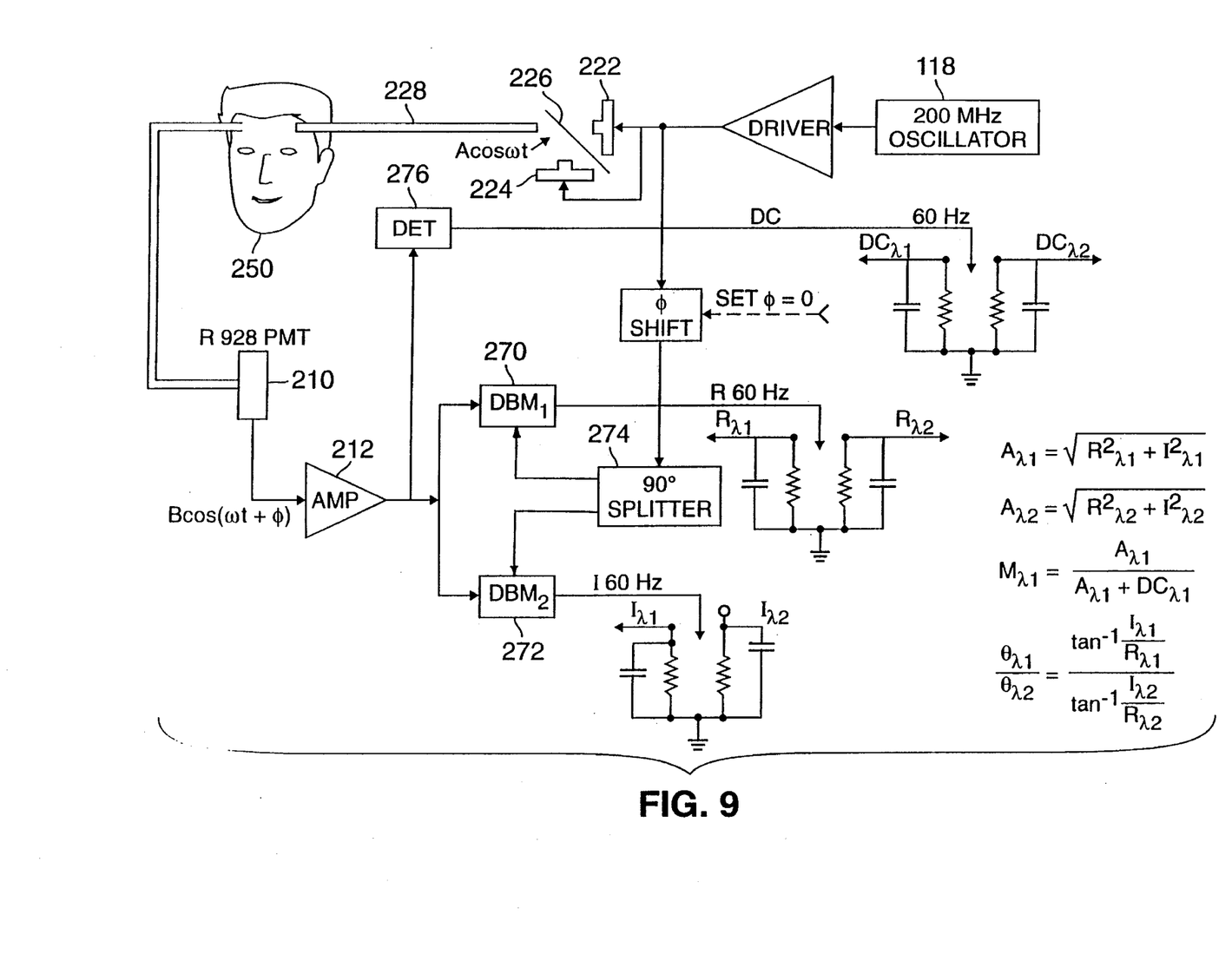
FIG. 9 is a block diagram of another embodiment of a phase modulation spectrophotometer.

In another embodiment, the pathlength corrected oximeter utilizes the same LED sources (22a, 22b, 22c) sinusoidally modulated at a selected frequency comparable to the average migration time of photons scattered in the examined tissue on paths from the optical input port of the LED's to the optical detection part of the photodiode detectors (24a, 24b, 24c), but the electronic circuitry is different. Referring to FIG. 9, this embodiment utilizes a 200 MHz precision oscillator 118 which drives two laser diodes 222, 224, again at 760 and 816 nm, the outputs of which are time shared into a fiber optic coupling 228 to the head 250. The detector output is put through two wide band double balance mixers (DBM) 270, 272 which are coupled through a 90° phase splitter 274 so that real (R) and imaginary (I) portions of the signal are obtained. The double balance mixers 270, 272 preferably operate at the modulation frequency. The phase ($\theta^\lambda$) is the angle whose tangent is the imaginary over the real part.

$$\theta^\lambda = \tan^{-1}\frac{I^\lambda}{R^\lambda} \qquad (8)$$

The amplitude is the square root of the sum of the squares of these values, providing the phase shift has been taken out as the residual phase shift θ set to zero.

$$A^\lambda = \sqrt{(R^\lambda)^2 + (I^\lambda)^2} \qquad (9)$$

This embodiment uses summing and dividing circuits to calculate the modulation index, which is the quotient of the amplitude over the amplitude plus the DC component obtained from a narrow band detector 276.

$$M^\lambda = \frac{A^\lambda}{A^\lambda + DC^\lambda} \qquad (10)$$

The phase processor receives the phase shifts for the phase and amplitude values for two or three wavelengths and calculates the ratio of the phase shifts.

For each wavelength, the phase shift and the DC amplitude are used to determine a selected tissue property, e.g., hemoglobin oxygenation.

Additional embodiments are within the following claims:

I claim:

1. A spectrophotometer for biological tissue examination, comprising:

a support structure adapted to be mounted on a subject including an optical input port located at a first location to introduce light to biological tissue of the subject;

an optical detection port located at a second location on said support structure spaced apart from said input port; and a barrier constructed and positioned to absorb photons directly propagating from said input port to said detection port;

an oscillator, including oscillator electronics, that generates a carrier waveform of a selected frequency comparable to an average migration time of photons scattered in tissue on paths from said optical input port to said optical detection port, said frequency being above 10 MHz;

a light source mounted on said support structure and connected to and receiving said carrier waveform from said oscillator, said light source generates light of a selected wavelength that is intensity modulated at said frequency and is introduced to the tissue of the subject at said input port;

a photodiode detector mounted on said support structure and connected to said detection port, said photodiode detector detects scattered light of said wavelength that has migrated in examined tissue of the subject between said input and detection ports;

a phase detector, including phase detector electronics, connected to receive signals from said oscillator and said diode detector, said phase detector measures a phase shift between said introduced light and said detected light that has migrated in the examined tissue over photon migration paths from said input port to said detection port; and a processor connected to receive said phase shift from said phase detector, said processor determines, based on said measured phase shift, a physiological property of the examined tissue dependent on tissue scattering and absorptive properties.

2. A spectrophotometer for biological tissue examination, comprising:

a support structure adapted to be mounted on a subject including an optical input port located at a first location to introduce light to biological tissue of the subject;

an optical detection port located at a second location on said support structure spaced apart from said input port; and a barrier constructed and positioned to absorb photons directly propagating from said input port to said detection port;

an oscillator, including oscillator electronics, that generates a carrier waveform of a selected frequency comparable to an average migration time of photons scattered in tissue on paths from said optical input port to said optical detection port, said frequency being above 10 MHz;

a light source mounted on said support structure and connected to and receiving said carrier waveform from said oscillator, said light source generates light of a selected wavelength that is intensity modulated at said frequency and is introduced to the tissue of the subject at said input port;

a photodiode detector, mounted on said support structure and connected to said detection port, said photodiode detector detects scattered light of said wavelength that has migrated in examined tissue of the subject between said input and detection ports and produces a detector signal;

a phase splitter, including a phase splitter circuit, that receives said carrier waveform and produces, first and second reference phase signals of predefined substantially different phases;

first and second double balanced mixers, including corresponding mixer circuits, that receive and correlate said reference phase signals and said detector signals to produce therefrom a real output signal and an imaginary output signal, respectively;

a processor connected to receive from said mixers said real output signal and said imaginary output signal, said processor determines from real output signal and an imaginary output signal a phase shift between said introduced light and said detected light; and said processor further determines, based on said phase shift, a physiological property of the examined tissue dependant on tissue scattering or absorptive properties.

3. The spectrophotometer of claim 2 wherein phase difference between said first reference phase signal and said second reference phase signal is 90 degrees.

4. A spectrophotometer for biological tissue examination, comprising:

a support structure adapted to be mounted on a subject including an optical input port located at a first location to introduce light to biological tissue of the subject;

an optical detection port located at a second location on said support structure spaced apart from said input port; and a barrier constructed and positioned to absorb photons directly propagating from said input port to said detection port;

a first oscillator, including oscillator electronics, that generates a carrier waveform of a first selected frequency comparable to an average migration time of photons scattered in tissue on paths from said optical input port to said optical detection port, said frequency being above 10 MHz;

a light source mounted on said support structure and connected to and receiving said carrier waveform from said oscillator, said light source generates light of a selected wavelength that is intensity modulated at said first frequency and is introduced to the tissue of the subject at said input port;

a photodiode detector mounted on said support structure and connected to said detection port, said photodiode detector detects light of said wavelength that has migrated in examined tissue of the subject between said input and detection ports and produces a detection signal at said first frequency corresponding to said detected light;

a second oscillator, including oscillator electronics, that generates a carrier waveform of a second frequency;

a reference mixer, including mixer electronics, connected to said first and second oscillators, said reference mixer generates a reference signal of a frequency approximately equal to the difference between said first and second frequencies;

a mixer, including mixer electronics, connected to receive signals from said second oscillator and said detection signal, said mixer converts said detection signal to a converted detection signal at said difference frequency;

a phase detector, including phase detector electronics, connected to receive reference signals from said reference mixer and said converted detection signal from said mixer, said phase detector measures a phase shift between said introduced light and said detected light that has migrated in the examined tissue over photon migration paths from said input port to said detection port; and a processor connected to receive phase shift signal from said phase detector, said processor determines, based on said measured phase shift, a physiological property of the examined tissue dependent on tissue scattering or absorptive properties.

5. The spectrophotometer of claim 1 or 4 further comprising:

a magnitude detector, including magnitude detector electronics, connected to said photodiode detector, said magnitude detector measures magnitude of said detected light, and two automatic gain controls connected to receive signals corresponding to said introduced light and said detected light, respectively, and level both said signals, both said leveled signals being introduced to said phase detector.

6. The spectrophotometer of claim 1 or 4 further comprising two automatic gain controls, including automatic gain control electronics, connected to receive signals corresponding to said introduced light and said detected light, respectively, and level both said signals, both said leveled signals being introduced to said phase detector.

7. The spectrophotometer of claim 1 or 4 further comprising:

said support structure further including
a second optical input port located at a second location and constructed to introduce light to the tissue; and
a second optical detection port located on said support structure spaced apart from said input ports;

a second light source, mounted on said support structure and connected to and receiving from said oscillator said carrier waveform, said second light source generates light of a second selected wavelength that is intensity modulated at said first frequency and is introduced to the tissue of the subject at said second input port;

a second photodiode detector mounted on said support structure and connected to said second detection port, said second photodiode detector detects light of said second wavelength that has migrated in the tissue of the subject between said second input port and said second detection port, respectively;

a second phase detector, including phase detector electronics, connected to receive a reference signal and a detection signal from said second photodiode detector and measure a phase shift between said introduced and said detected light at said second wavelength; and said processor further connected to receive from said second phase detector a second phase shift at said second wavelength, said first and second phase shifts being subsequently used for determination of said physiological property.

8. The spectrophotometer of claim 7 further comprising:

a first and a second magnitude detector, including corresponding magnitude detector electronics, connected to said first and second photodiode detectors, respectively, said magnitude detectors measure magnitude of said detected light at each of said wavelengths, and said processor further connected to receive from said first and said second magnitude detector said magnitudes for determination of said physiological property.

9. The spectrophotometer of claim 7 further comprising:

said support structure further including
a third optical input port located at a third location and constructed to introduce light to the tissue; and
a third optical detection port located on said support structure spaced apart from said input ports;

a third light source mounted on said support structure and connected to said oscillator, said third light source generates light of a third selected wavelength that is intensity modulated at said first frequency and is introduced to the tissue of the subject at said third input port;

a third photodiode detector mounted on said support structure and connected to said third detection port, light of said third wavelength that has migrated in the tissue of the subject between said third input port and said third detection port, respectively;

a third phase detector, including phase detector electronics, connected to receive a reference signal and a detection signal from said third photodiode detector, said third phase detector measures a phase shift between said introduced and said detected light at said third wavelength; and said processor further connected to receive phase shift at said third wavelength from said third phase detector, said first, second and third wavelength phase shifts being subsequently used for determination of said physiological property.

10. The spectrophotometer of claim 9 wherein each said photodiode detector is a PIN diode.

11. The spectrophotometer of claim 9 wherein each said photodiode detector is an avalanche diode.

12. The spectrophotometer of claim 9 further comprising:

a first, a second and a third magnitude detector, including corresponding magnitude detector electronics, connected to said first, second and third photodiode detectors, respectively, said magnitude detectors measure magnitude of said detected light at each of said wavelengths; and said processor further connected to receive said magnitudes for determination of said physiological property.

13. The spectrophotometer of claim 9 wherein each said light source is a light emitting diode and said selected wavelength is in the visible or infra-red range.

14. The spectrophotometer of claim 9 wherein each said photodiode detector further comprises a substantially single wavelength filter.

15. The spectrophotometer of claim 1, 2 or 4 further comprising:
a low frequency oximeter, including a corresponding circuit, removably connected to said source and said photodiode, said low frequency oximeter controls introduction of low frequency modulated light at said wavelength, and detection of light that has migrated from said input port to said detection port in the examined tissue
said processor removably connected to said low frequency oximeter and further constructed to receive absorption values from said oximeter for determination of said physiological property.

16. The spectrophotometer of claim 15 wherein said processor is programmed to calculate, based on said measured phase shift, an average pathlength of photons migrating from said input port to said detection port in the examined tissue and utilize said pathlength for calibrating said absorption values from said low frequency oximeter.

17. The spectrophotometer of claim 1, 2 or 4 further comprising:
a magnitude detector, including magnitude detector electronics, connected to said photodiode detector, said magnitude detector measures magnitude of said detected light, and
said processor further connected to and receiving from said magnitude detector magnitude data for determination of said physiological property.

18. The spectrophotometer of claims 1, 2 or 4 wherein said light source is a light emitting diode and said selected wavelength is in the visible or infra-red range.

19. The spectrophotometer of claims 1, 2 or 4 wherein said photodiode detector is a PIN diode.

20. The spectrophotometer of claims 1, 2 or 4 wherein said photodiode detector is an avalanche diode.

21. The spectrophotometer of claims 1, 2 or 4 wherein said photodiode detector further comprises a substantially single wavelength filter.

22. The spectrophotometer of claim 1, 2 or 4 further comprising:
a second optical input port coupled to said support structure located at a second location and constructed to introduce light to the examined tissue;
a second light source mounted on said support structure and connected to said oscillator, said second light source generates light of a second selected wavelength that is intensity modulated at said first frequency and is introduced to the tissue of the subject at said second input port;
said photodiode detector including a second photodiode that further detects alternately, at said detection port, light of said first and second wavelengths that have migrated in the tissue of the subject between the first and said second input ports and said detection port, respectively;
said phase detector further receives alternately from said diode detector signals corresponding to said detected light of said first and second wavelengths; and
said processor further receives alternately phase shifts at said first and second wavelengths from said phase detector, said phase shifts being subsequently used for determination of said physiological property.

23. The spectrophotometer of claim 22 further comprising:
a magnitude detector, including magnitude detector electronics, connected to said photodiode detector, said magnitude detector measures magnitude of said detected light at each of said wavelengths, and
said processor further connected to and receiving from said magnitude detector said magnitudes for determination of said physiological property.

24. The spectrophotometer of claim 1, 2 or 4 further comprising a readout device, worn by said subject, for displaying data of said processor related to said physiological property.

25. The spectrophotometer of claim 1, 2 or 4 further comprising a telemetry apparatus for sending acquired data to a remote location.

26. The spectrophotometer of claim 1, 2 or 4 wherein said frequency of said oscillator is about 50.1 MHz.

27. The spectrophotometer of claim 1, 2 or 4 wherein said oscillator is constructed to maintain long term stability of operation.

28. The spectrophotometer of claim 1, 2 or 4 wherein said physiological property of the examined tissue is related to levels of one of the following: myoglobin, hemoglobin oxygenation, cytochrome iron, cytochrome copper, melanin and glucose in the examined tissue.

29. The spectrophotometer of claim 1, 2 or 4 wherein said physiological property is a scattering coefficient ($\mu_s$) of the examined tissue.

30. The spectrophotometer of claim 1, 2 or 4 wherein said physiological property is an absorption coefficient ($\mu_a$) of the examined tissue.

* * * * *